United States Patent
Schlafer (10) Patent No.: US 8,012,741 B2
(45) Date of Patent: Sep. 6, 2011

(54) BIOGAS MEASURING DEVICE AND METHOD FOR MEASURING BIOGAS VOLUMES

(75) Inventor: Ottmar Schlafer, Wildemann (DE)

(73) Assignee: Clausthaler Umwelttechnik Institut (GmbH) (Cutec-Institut), Clausthal-Zellerfeld (DE)

( * ) Notice: Subject to any disclaimer, the term of this patent is extended or adjusted under 35 U.S.C. 154(b) by 976 days.

(21) Appl. No.: 11/575,631

(22) PCT Filed: Sep. 28, 2005

(86) PCT No.: PCT/DE2005/001725
§ 371 (c)(1),
(2), (4) Date: Oct. 19, 2007

(87) PCT Pub. No.: WO2006/034699
PCT Pub. Date: Apr. 6, 2006

(65) Prior Publication Data
US 2008/0121019 A1   May 29, 2008

(30) Foreign Application Priority Data
Sep. 30, 2004   (DE) .......................... 10 2004 047 560

(51) Int. Cl.
*C12M 1/36*   (2006.01)
*C12M 1/34*   (2006.01)
*C12M 3/00*   (2006.01)

(52) U.S. Cl. ................. 435/286.1; 435/287.2; 435/287.5

(58) Field of Classification Search ............... 435/287.5, 435/286.1, 287.2
See application file for complete search history.

(56) References Cited

U.S. PATENT DOCUMENTS
4,750,454 A * 6/1988 Santina et al. ................... 123/3
(Continued)

FOREIGN PATENT DOCUMENTS
DE          3540481 A1    9/1986
(Continued)

OTHER PUBLICATIONS

Jochen Buchs et al., RAMOS (Respiration Activity MOnitoring System, online BIO forum, Mar. 2001, pp. 149-151.
(Continued)

*Primary Examiner* — Robert J Warden
(74) *Attorney, Agent, or Firm* — Whitham Curtis Christofferson & Cook, PC (57) ABSTRACT

The invention relates to a biogas measuring device comprising a bioreactor (9); a gas volume measuring appliance (2) which is connected to the bioreactor (9) in a communicating manner by means of a gas line (11) for biogas; a stirring machine (10) guided in the bioreactor in a gas-tight manner, and a measurement, control and evaluation unit for controlling the biogas measuring device and determining the gas volume (V) produced in the bioreactor according to gas volumes ($\Delta V$) of consecutive measuring cycles, measured by means of the gas volume measuring appliance (2). The inventive biogas measuring device is characterized in that the bioreactor (9) is outwardly sealed in a gas-tight manner in such a way that all gas volumes produced in the bioreactor (9) can be recorded by the measuring chamber (3) of the gas volume measuring appliance (2); a cooling element is provided on the gas line (11) for the biogas; and the measurement, control and evaluation unit is used, in each measuring cycle, to introduce a gas quantity into the measuring chamber (3) by opening the gas inlet valve (12) until a defined threshold gas pressure is reached, to close the gas inlet valve (12) when a defined threshold gas pressure is reached, to measure the temperature (Ti) in the measuring chamber (3), to open the gas outlet valve (14) for a relief time, and to close the gas outlet valve (14), and to control the biogas measuring device, in such a way that the cooling element is controlled in order to reduce the water vapor concentration in the biogas by condensation, and the measured gas volume ($\Delta V$) of a measuring cycle is standardized to standard conditions.

19 Claims, 6 Drawing Sheets

U.S. PATENT DOCUMENTS

| | | | |
|---|---|---|---|
| 5,470,745 A * | 11/1995 | Beteau et al. | 435/286.1 |
| 5,742,523 A | 4/1998 | Thomas et al. | 364/558 |
| 2002/0022260 A1 * | 2/2002 | Ishii | 435/286.1 |
| 2008/0152967 A1 * | 6/2008 | Roychowdhury | 429/13 |
| 2009/0305379 A1 * | 12/2009 | Johnson et al. | 435/170 |

FOREIGN PATENT DOCUMENTS

| | | |
|---|---|---|
| DE | 101 62 286 A1 | 7/2003 |
| EP | 0 021 470 A | 1/1981 |
| EP | 0 021 470 A1 | 1/1981 |
| EP | 0 497 414 A1 | 1/1992 |
| EP | 497 414 A | 8/1992 |
| FR | 2 767 206 | 5/1997 |

OTHER PUBLICATIONS

A International Preliminary Search Reaport issued by the International Bureau of WIPO pp. 1 to 195.

* cited by examiner

BIOGAS MEASURING DEVICE AND METHOD FOR MEASURING BIOGAS VOLUMES

The invention relates to a biogas measuring device with
a bioreactor,
a gas volume meter connected communicatingly to the bioreactor via a gas conduit for biogas, with:
   a measuring chamber which has a defined measurement volume in a housing,
   a gas inlet into the measuring chamber, said gas inlet being controlled by a gas inlet valve,
   a gas outlet from the measuring chamber, said gas outlet being controlled by a gas outlet valve,
   a pressure sensor for detecting the atmospheric pressure,
   a differential pressure sensor, communicating with the measuring chamber, for detecting the differential pressure between the gas pressure in the measuring chamber and the atmospheric pressure or a current system pressure,
and with
   a measurement, control and evaluation unit which is set up for controlling the biogas measuring device and determining the gas volumes generated in the bioreactor as a function of gas volumes, measured by the gas volume meter, of successive measurement cycles, with the steps for each measurement cycle of:
      a) introduction of a gas quantity into the measuring chamber by opening the gas inlet valve until a defined threshold gas pressure is reached,
      b) closing of the gas inlet valve when a defined threshold gas pressure is reached,
      c) measurement of the temperature in the measuring chamber,
      d) opening of the gas outlet valve for an expansion time, and
      e) closing of the gas outlet valve.

The invention relates, furthermore, to a method for measuring biogas volumes generated in a bioreactor, with a multiplicity of measurement cycles, by means of such a biogas measuring device.

Gas volume meters are known in the form of displacement gas meters, differential-pressure gas meters and flow gas meters.

Displacement gas meters are volumetric meters in which volume measurement takes place directly by the periodic filling and emptying of one or more measuring chambers. In this case, the physical property of the gas is utilized in order to fill any surrounding space completely. The part volumes or fillings of the measuring chambers are added together by a counter. The gas volume which has flowed through corresponds in this case to the number of fillings times and the measuring chamber content.

All displacement gas meters are independent of the flow profile. They measure the gas volume in the operating state, that is to say with the actual values for pressure and temperature. The pressure difference between the inlet and outlet of the meter serves as the drive force for these gas meters. The drive energy is extracted from the gas stream. This category includes wet drum gas meters which, because of their high precision and the small measurement range, are employed predominantly in the laboratory and calibration sector. Drum gas meters are too costly for industrial use and because a check of the confining liquid is necessary daily, they are too maintenance-intensive. Positive-displacement gas meters are an alternative. Furthermore, known displacement gas meters are rotary-piston and rotary-sluice gas meters which are highly robust, but, because of the gap losses due to the type of construction and on account of the pulsations generated, are suitable only for high gas volume flows.

Differential-pressure gas meters consist of a measurement section with a differential-pressure transducer (diaphragm or nozzle) and a throughflow measurement-quantity converter. At the throttles built into the pipeline, an increase in flow velocity occurs as a result of the cross-sectional narrowing. The pressure difference (effective pressure) occurring thereby is a measure of the throughflow.

In flow gas meters, volume measurement takes place indirectly by means of measurement members moved by the flow or immovable measurement members influenced periodically. Volume measurement is based on velocity measurement. A distinction is made between turbine-wheel meters, in which a wheel provided with blades is set in rotation by flow forces, and vortex gas meters, in which periodic flow vortices generated by corresponding fittings are used for counting. The rotational frequency of the turbine wheel or the vortex frequencies are proportional to the mean flow velocity and consequently to the volume throughflow. Flow gas meters also include ultrasonic meters.

In the fermentation of biomass, gas generation takes place according to the biological decomposition of the organic compounds and to the increase in the gas-producing cellular mass in an "S"-shaped curve profile. After a steep rise in gas generation up to a maximum, this is followed by a flattening of the gas curve due to the decline of gas generation to the end of fermentation. This gives rise to a volume flow which, in the course of fermentation, varies by several powers of ten and, toward the end of fermentation, amounts to only a few milliliters per day (ml/d). On account of the losses due to gap dimensions, internal resistances and unsteady flow, such a low volume flow cannot be detected by open systems, such as differential-pressure and flowmeters, or rotary-sluice and rotary-piston meters. The known closed drum and positive-displacement meters are also unsuitable on account of the wide measurement range and the drive energy of the systems which is required from the gas stream and the associated pressure rise in a test reactor.

A particular feature of the gas measurement of low maximum volume flows of about $q_{max} < 650$ m³/h and with low effective pressures of about $P_{\textit{eff}} < 100$ hPa is the fact that the determination of the standard volume $V_n$ does not have to take place by means of a converter, but can be achieved solely by recalculations of the operating volume by means of correcting factors.

Büchs J. and Anderlei T.: "RAMOS (Respiration Activity Monitoring System)—Online—Messung der Atmungs-aktivitäten biologischer Kulturen in geschüttelten Bioreaktoren [—Online—Measurement of respiration activities of biological cultures in shaken bioreactors], in BIOforum 3/2001, pages 149 to 151, describe a method for detecting the respiration activity of biological cultures in shaken bioreactors. During a culture test in the shaken flasks, a recurring measurement cycle is run through continuously and is subdivided into a measurement phase and a scavenging phase. In the scavenging phase, an inlet and an outlet valve are opened, and scavenging gas flows through the measuring flask. To start the measurement phase, the inlet and the outlet valve of the measuring flask are closed. The persistent respiration activity of the microorganisms leads to variations in the oxygen and carbon dioxide partial pressure in the gas space of the measuring flask. An oxygen transfer rate (OTR) and carbon dioxide transfer rate (CTR) and also a respiration quotient (RQ) in the measuring flask are determined from the partial pressure changes which are detected with the aid of an oxygen and carbon dioxide sensor. The valves are subsequently opened again, and the next measurement cycle commences. A gas volume which would be generated by the biomass cannot be determined.

In gas volume measurement particularly for optimizing the biogas yield during the fermentation of biomass in a bioreactor, a relatively wide measurement range is required because of the characteristic of biological gas release in discontinuous tests, so that larger volume flows in the milliliter range per minute can be measured at the commencement of fermentation and low volume changes of a few milliliters per day can be measured at the end. In this case, the biological process should not be influenced. In particular, no appreciable pressure should arise in the test reactor. On account of the resulting low pressure drop, the low volume flow and the high requirements as to long-term leaktightness, none of the open gas measurement systems driven mechanically by the gas stream are suitable.

U.S. Pat. No. 5,742,523 A discloses a measuring device for gas volumes, with a gas container of known volume which has an inlet valve for gas in order to fill up the vessel with gas until an initial pressure is reached. After the measurement of the temperature of the container and of the gas pressure in the container, the gas pressure in the container is calculated via an outlet valve and a gas conduit, and the outlet valve is opened until the calculated gas pressure is reached. In this case, the gas temperature is kept constant. A most accurately defined mass of gas can thereby be discharged through the outlet valve.

FR 2 767 206 discloses a gas measuring device, in which a gas quantity is introduced into a defined volume via an inlet valve. By the temperature and the gas pressure in the volume being measured, the gas quantity in the volume is determined.

Furthermore, DE 101 62 286 A1 describes a device for determining the gas volume under ambient pressure, with a measuring chamber, a pressure sensor for detecting the internal pressure in the measuring chamber, a pressure sensor for detecting the ambient pressure and a temperature sensor. With the aid of inlet and outlet valves, gas volumes are passed through the measuring chamber, and their respective gas volumes are determined, using Boyle's Law, according to the formula $p_1*V_1/T_1=p_2*V_2/T_2$, $p_1$ being the pressure prevailing in the measuring chamber, $V_1$ being the volume of the measuring chamber, $T_1$ being the temperature in the measuring chamber, $p_2$ being the ambient pressure, $V_2$ being the gas volume sought and $T_2$ being the ambient temperature.

The object of the invention is to provide a biogas measuring device, by means of which biogas volumes generated in a biogas reactor over a long period of observation can be determined with high accuracy.

The object is achieved by means of a generic biogas measuring device in that
  the bioreactor is closed off, outwardly gastight, such that all the gas volumes generated in the bioreactor can be detected by the measuring chamber of the gas volume meter,
  an agitator is guided, gastight, in the bioreactor,
  a cooling element is provided on the gas conduit for the biogas, and the measurement, control and evaluation unit for controlling the biogas measuring device is designed in such a way that the cooling element is activated in order to reduce the water vapor concentration in the biogas due to condensation and the measured gas volume of a measurement cycle is normalized to standard conditions.

By means of such a biogas measuring device, individual volume elements can first be measured and subsequently extracted from a hermetically closed-off system, while the pressure conditions can be kept approximately constant. In this case, a gas volume meter known from DE 101 62 286 A1 is used, with a measurement principle based essentially on a measuring chamber which can be connected directly to a bioreactor via gas conduits, the internal pressure in the measuring chamber being measured by a sensitive pressure sensor. When the pressure in the system reaches a set low threshold value, the measuring chamber is separated from the sample space, that is to say from the bioreactor, by means of a valve, and the included gas volume is determined. The cell is subsequently expanded to ambient pressure by the opening of a gas outlet valve and the gas is released from the system. After the closing of the outlet valve, the connection to the bioreactor is restored and the measurement cycle can commence from the outset.

The biogas measuring device according to the invention is a closed-off measuring system for biogas generation, preferably on a laboratory scale, in which the gas pressure meter is connected communicatingly to a bioreactor and the system is closed off, outwardly gastight, such that all the gas volumes generated in the bioreactor can be detected by the measuring chamber of the gas volume meter and are passed out through the gas volume meter in a controlled way. An agitator is in this case guided, gastight, in the bioreactor, in order to mix the biomass in the bioreactor. Furthermore, a cooling element on the gas conduit for biogas, led from the bioreactor to the gas volume meter, is provided, in order to reduce the water vapor concentration in the biogas due to condensation and thereby to ensure comparable measurement conditions.

Furthermore, what is achieved by normalization to standard conditions is that the exact profile of volume generation can be recorded over time, not merely sum volumes between measurements lying far apart.

These measures, taken together, lead to the biogas capacity of a biogas reactor being detectable with high accuracy, even when there are only low biogas volume flows.

The following are required for the measurement of a reproducible biogas volume:
a) A bioprocess (monitoring, regulation) kept constant
  The biological process and consequently gas production depend essentially on the biological parameters of the biomass used and on the micro-organisms employed, the physical parameters of temperature, intermixing and dry substance content and the chemical parameters of pH value, redox potential, illumination, organic acids, etc. The change in all these parameters has an influence on the biological process and therefore on gas production and on the result of gas measurement. The chemical and biological parameters are therefore set at constant before the tests are set up. However, the physical parameters have to be regulated and monitored during the running time of the tests and have to be taken into account in evaluating the tests. The biogas measuring device fulfilling these requirements therefore provides a regulated and monitored temperature, a regulated and monitored agitator and condensation and recirculation of the water vapor out of the measurement gas back into the biomass.
b) Measurement under constant conditions (standardization)
  For this purpose, water vapor is removed from the measurement gas (drying).
c) Account taken of the ambient parameters (normalization)
  In the biogas measuring device according to the invention, the ambient temperature and the ambient pressure are measured and taken into account.
  By contrast, in conventional laboratory biogas meters, the parameters of the connected biological process or the ambient conditions are not taken into account for evaluating the gas measurement data.

The gas volume is calculated on the assumption of an ideal gas by the pressure in a constant volume being detected. This volume should not vary in the event of a change in the gas pressure, so that the measuring chamber must be of relatively rigid design.

It is advantageous if the measurement, control and evaluation unit is designed for measuring a current system pressure after the closing of the gas outlet valve and if there is a standby phase for adapting the defined threshold gas pressure for a following measurement cycle with respect to the current system pressure. The defined threshold gas pressure may be, for example, about two hPa above the current system pressure. That is to say, when the differential pressure sensor detects a rise in pressure after the start of a measurement cycle by the amount of the defined relative threshold pressure, the gas volume at this time point is determined after the gas inlet valve has been closed.

The heat capacity of the housing which surrounds the measuring chamber should be very much higher than the heat capacity of the gases to be measured. Moreover, the mass of the housing should be very much greater than the mass of the gas capable of being received by the measuring chamber. This ensures as high a temperature constancy as possible, in that rapid temperature changes of the gas due to thermal coupling to the measurement cell are compensated.

In order further to optimize the thermal coupling to the measurement cell, it is advantageous if the measuring chamber is filled with steel wool or the like.

It is advantageous, furthermore, if a scavenging gas inlet, controlled by a scavenging gas valve, is provided in the measuring chamber, in order to introduce a scavenging gas, such as, for example, nitrogen, into the measuring chamber in a scavenging phase.

The measurement, control and evaluation unit is preferably designed for determining the gas volume of a measurement cycle from the atmospheric pressure, the differential pressure and the defined measurement volume according to the formula:

$$\Delta V = \left(\frac{P_a + dP}{P_a} - 1\right) V_{REF}.$$

The differential pressure used is preferably the difference of the gas pressure measured in the measurement cycle after the threshold gas pressure is reached in the measuring chamber and of the system pressure determined in the preceding measurement cycle.

Normalization may take place by the calculation of a gas volume normalized to a standard pressure, preferably $P_N = 1013.25$ hPa, according to the relation $$\Delta V_n = \frac{P_1 \cdot \Delta V}{P_n}$$

by means of the measured pressure $P_1$ in the measuring chamber when the defined threshold gas pressure is reached.

It is also advantageous, however, to calculate a gas volume normalized to the standard temperature, preferably with a standard temperature of 20° C., according to the relation $$\Delta V_n = \frac{\Delta V \cdot T_n}{T_1}$$

by means of the measured temperature $T_1$ of the measuring chamber.

Furthermore, the measurement, control and evaluation unit is preferably designed for integrating the gas volumes determined in successive measurement cycles or normalized gas volumes. The gas volume generated in a closed-off system can consequently be detected over a long time, even if gas generations are low.

Preferably, the agitator has integrated gas conduits for measurement gas and scavenging gas, a cylindrical body with lateral bores for the gas conduits and a central bore for receiving an agitating shaft, an agitating motor received, gastight, in the body, and a cone on the body for gastight installation in the bioreactor. The gas conduit for the measurement gas is in this case connected to the gas volume meter. The gas supply conduit for scavenging gas is preferably led into the bioreactor through the agitating shaft designed as a hollow shaft.

To reduce the water vapor concentration in the measurement gas due to condensation, a Peltier cooling element is preferably provided in the agitator on the gas conduit for the measurement gas. The Peltier cooling element can be pressed directly onto a head of the agitator, for example by means of a special heat conduction film.

The object is achieved, furthermore, by means of a method for measuring biogas volumes generated in a bioreactor, by means of such a biogas measuring device, with a multiplicity of measurement cycles, in that for each measurement cycle are carried out the steps of:

a) cooling of the biogas in order to reduce the water vapor concentration in the biogas,
b) introduction of a gas quantity of biogas into the measuring chamber (3) by opening the gas inlet valve (12) until a defined threshold gas pressure is reached,
c) closing of the gas inlet valve (12) when a defined threshold gas pressure is reached,
d) measurement of the temperature ($T_1$) in the measuring chamber (3),
e) opening of the gas outlet valve (14) for an expansion time, and
f) closing of the gas outlet valve (14),
g) normalization of the measured gas volume ($\Delta V$) of a measurement cycle to standard conditions.

Advantageous embodiments of the method according to the invention are described in the subclaims.

The invention is explained in more detail below, by way of example, with reference to the accompanying drawings in which.

Figure 1:
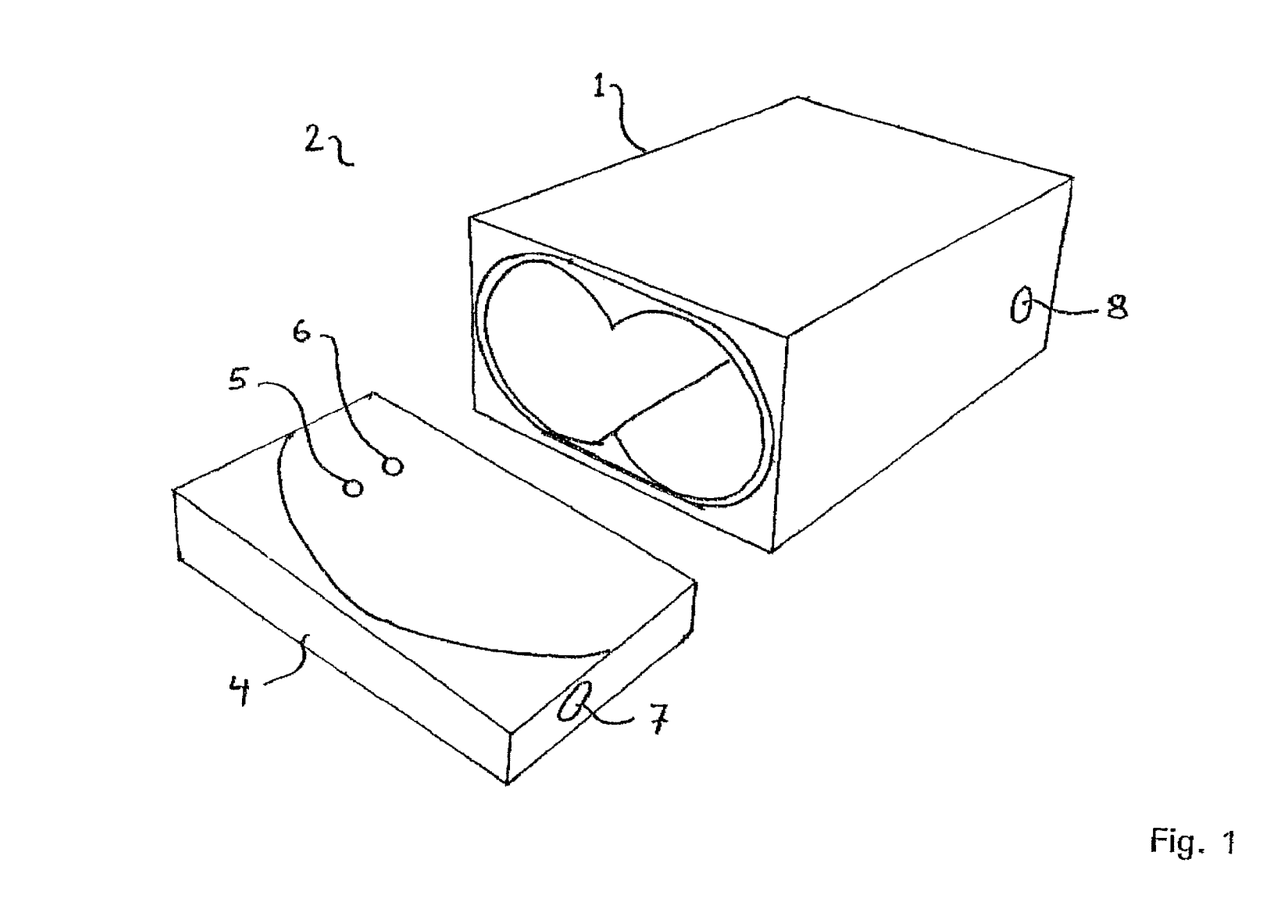
FIG. 1 shows a perspective view of a housing for a gas volume meter used in the biogas measuring device.

FIG. 1 shows a perspective view of a housing 1 for a gas volume meter 2. The housing 1 has provided in it a measuring chamber 3 in the form of two cylindrical bores lying next to one another and merging one into the other. The measuring chamber 3 is closed, leaktight, by means of a front plate 4. An O-ring seal in a groove in the housing 1 or the front plate 4 may be provided for this purpose.

In the front plate 4 are provided a bore for a gas inlet 5 and a bore for a gas outlet 6 and also a leadthrough bore 7 for scavenging gases.

Furthermore, a differential pressure sensor 8 is screwed into the housing 1 and communicates with the measuring chamber 3 such that the internal pressure in the measuring chamber 3 with respect to the atmospheric pressure $P_a$ is detected. To detect the lowest possible pressure differences dP, preferably the diaphragm of the pressure sensor 8 is sealed off, with low tension, with respect to the surroundings by means of high-grade elastomers. Such elastomers may be, for example, Keltan, Dutral, Viton and Teflon. These elastomers are also sufficiently resistant to the corrosive properties of biogases.

The housing 1 preferably consists of a solid V.sub.4A block, for example having the outer dimensions of 75.times.50.times.30 mm. With a defined volume of 63 cm$^3$ being milled out, the housing 1 has a mass of 456 g. These dimensions are advantageous in order to smooth out the temperature fluctuations of the measurement gas when the measurement cell is in operation. The gas is compressed slightly until a threshold gas pressure of, for example, 2 hPa above the atmospheric pressure $P_a$ or a current system pressure $P_2$ is reached. Since this operation proceeds very slowly, the compression heat can be discharged so that the measurement gas does not heat up. During subsequent rapid expansion, however, the gas cools down. When the outlet valve is then closed, the gas mass included in the measuring chamber 3 is overcooled. However, the pressure rise which took place during subsequent heat exchange results from the heat supplied from outside, not from an actual change in volume. The system would consequently no longer be closed and volume calculation would not be possible.

In the gas volume meter 2, therefore, another solution is implemented, in which the cooling of the gas inside it is greatly reduced. On account of the very much higher heat capacity of $V_4A$, as compared with the heat capacity of the measurement gas, and a very much greater mass of the measurement cell, as compared with the mass of the measurement gas, it may be assumed that, in the case of a correspondingly large surface of the measurement cell, the overcooled measurement gas heats up again, without appreciably cooling the measurement cell. By the measuring chamber 3 being filled with $V_4A$ steel wool and due to the associated enormous increase in the inner surface of the gas space, the measurement gas is in rapid temperature exchange with the solid steel block of the housing 1, so that temperature fluctuations subsequently no longer occur. The time required for a measurement cycle can thereby be shortened to 500 ms.

When the measuring chamber 3 is milled out, a middle web is left, in order to ensure as high a mechanical stability of the housing 1 as possible.

Figure 2:
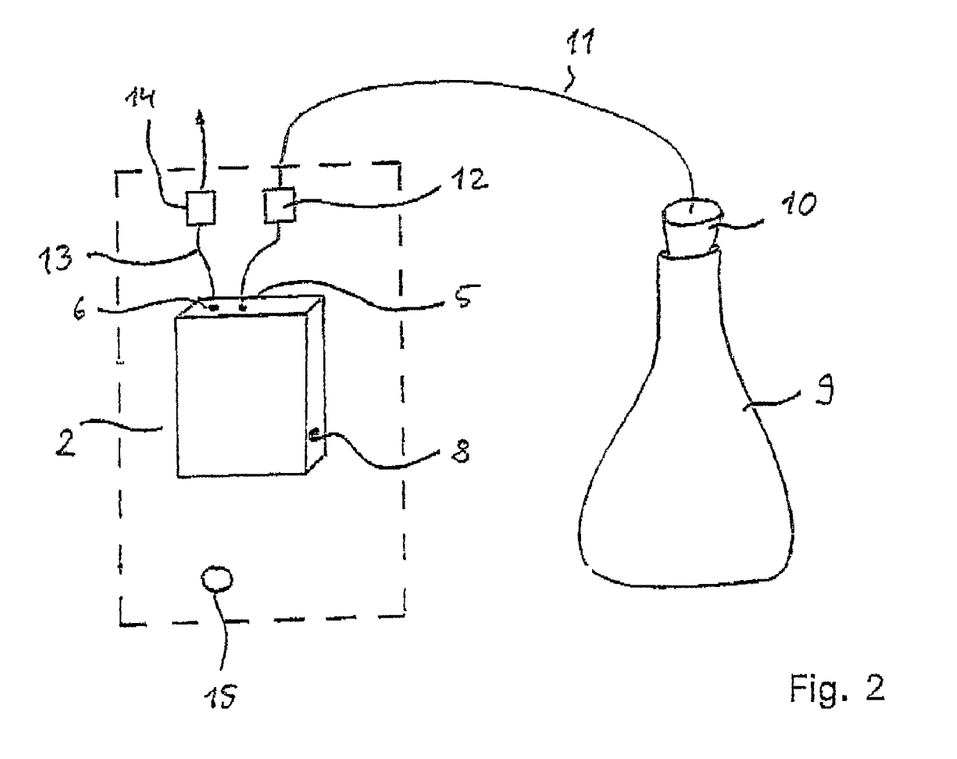
FIG. 2 shows a sketch of a gas volume meter connected to a bioreactor.

FIG. 2 reveals the use of the measurement cell shown in FIG. 1 in conjunction with a bioreactor 9. The bioreactor 9 is, for example, an Erlenmeyer flask into which an agitator 10 is introduced, gastight. A gas discharge hose 11 is led via a gas inlet valve 12 to the gas inlet 5 of the measurement cell. Connected to the gas outlet 6 is a gas outlet conduit 13 which is led into the atmosphere via a gas outlet valve 14.

Furthermore, a pressure sensor 15 for detecting the atmospheric pressure $P_a$ is also provided.

Figure 3:
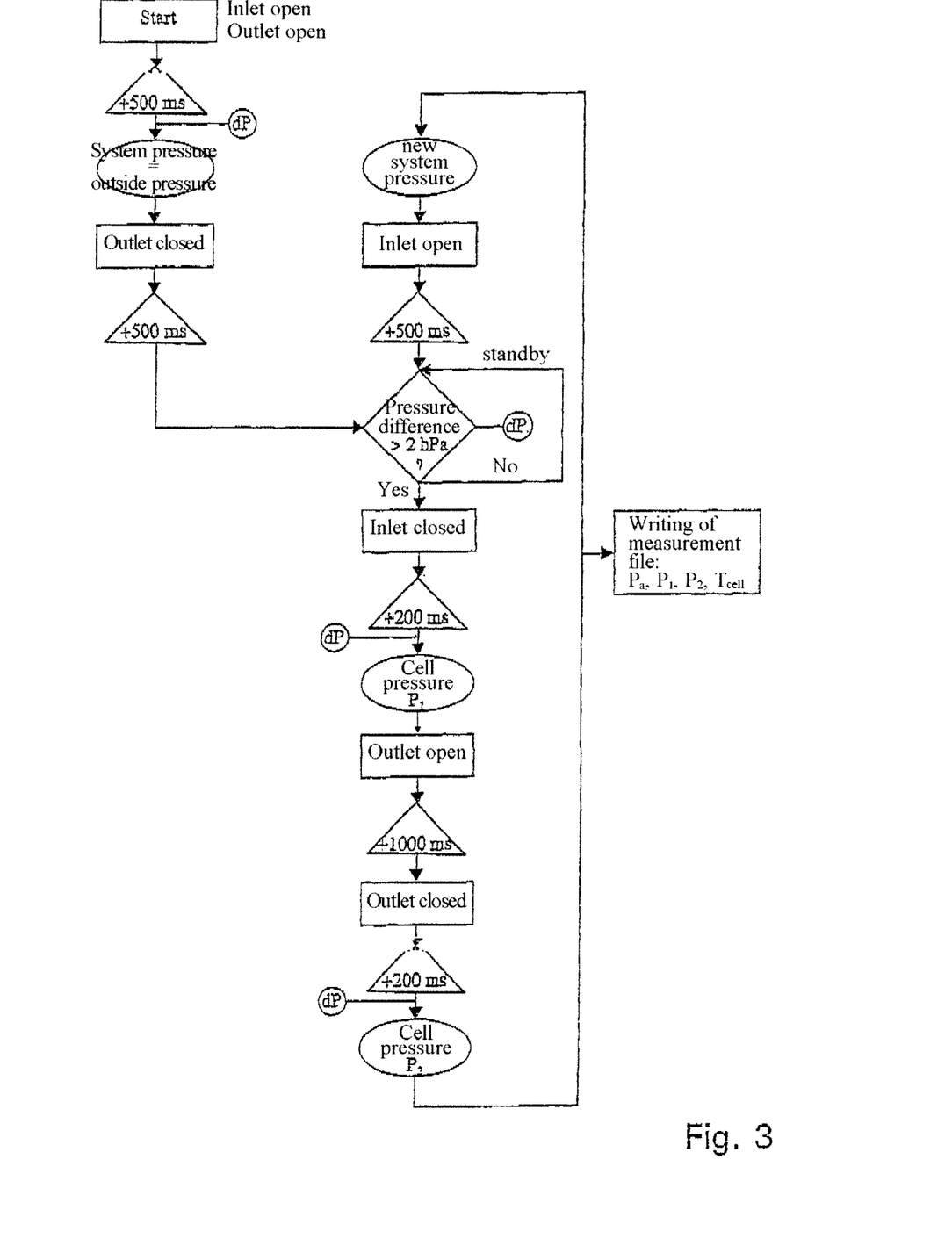
FIG. 3 shows a flowchart of the flow control of a measuring operation.

Carrying out a measurement by means of such a system is explained by means of FIG. 3 which shows a flowchart of the flow control of the measuring operation. Measurement is carried out repeatedly for successive measurement cycles.

First, in an initializing step, the gas inlet valve 12 and the gas outlet valve 14 of the measurement cell are opened. In this position, 5 seconds after the start of the test, the measurement of the relative internal pressure dP in the measuring chamber 3 takes place once in order to detect a current system pressure $P_2$ and in order to calibrate the system.

After the closing of the gas outlet valve 14, the switching and measuring step 1 commences. The measuring chamber 3 in this case forms with the bioreactor 9 a closed outwardly gastight space. After a pressure time of 500 ms has elapsed, the pressure sensor 8 begins to record the pressure changes in the measuring chamber 3, that is to say in the enclosed gas space, and to compare them with a preset threshold gas pressure. This pressure threshold may be set, for example, at +2 hPa. When this threshold gas pressure is reached, the gas inlet valve 12 is closed and a switching measuring step 3 commences. After 200 ms, a measurement of the relative pressure $P_1$ in the measuring chamber 3 with respect to the atmospheric pressure $P_a$ takes place. The included gas volume is defined at this time point by the known parameters of pressure $P_1$, temperature $T_1$ and volume V. In a switching and measuring step 3, the gas outlet valve 14 is opened for a duration of 1000 ms, in order to expand the outflowing gas as fully as possible.

The switching and measuring step 4 commences with the closing of the gas outlet valve 14, and after 200 ms the second measurement of the relative pressure $P_2$, in this case at the lower pressure level, takes place. This lower pressure level is used as the new system pressure $P_2$ for calculating the threshold gas pressure for the next measurement cycle. As a rule, the system pressure $P_2$ is near the atmospheric pressure $P_a$ of the external surroundings, but may, for example, assume different values at the gas outlet valve 14 due to counterpressure, without the result being influenced.

In this fourth step, all the average values of individual measurements of the temperature $T_1$ in the measuring chamber 3, of the relative differential pressure $dP=P_1-P_2$ and of the atmospheric pressure $P_a$ can be written into a measurement file.

The gas inlet valve 12 is subsequently opened again, with the result that the switching and measuring step 1 commences again for a new measurement cycle.

The calculation of each individual gas volume dV takes place according to the equation $$dV = \left(\frac{P_a + (P_1 - P_2)}{P_a} - 1\right)V_{REF},$$

$P_a$ being the atmospheric pressure, $P_1$ being the relative pressure $P_1$ measured in the switching and measuring step 2, $P_2$ being the current system pressure and $V_{REF}$ being the defined known volume of the measuring chamber 3.

In this case, the atmospheric pressure $P_a$ is measured currently for each measurement cycle, so that a change in the relative air pressure does not lead to an incorrect measurement.

The biogas volume $V_{ges}$ generated overall in the bio-reactor 9 is composed of the sum of the individual volumes dV determined in each measurement cycle:

$$V_{ges} = \Sigma_t dV(t).$$

The individual gas volumes dv or the overall gas volume $V_{ges}$ can be normalized to standard conditions. It is thereby possible to obtain comparable results.

The gas volume $V_n$ normalized to the standard pressure $P_n$ is calculated from the measured pressure $P_1$ and the standard pressure $P_n$ of 1013.25 hPa according to the formula:

$$V_2 = \frac{P_1 \cdot V_1}{P_2},$$

a temperature $T_1$ in the measuring chamber 3 equal to the standard temperature $T_n$ of 20° C. being assumed.

The gas volume $V_2$ normalized to the standard temperature $T_n$ of 20° C. is calculated, in the case of a measured pressure $P_1$ corresponding to the standard pressure $P_n$ of 1013.25 hPa, according to the formula:

$$V_n = \frac{V_1 \cdot T_n}{T_1}.$$

The normalized gas volume $V_2$ is given in normal liters $N_1$.

Figure 4:
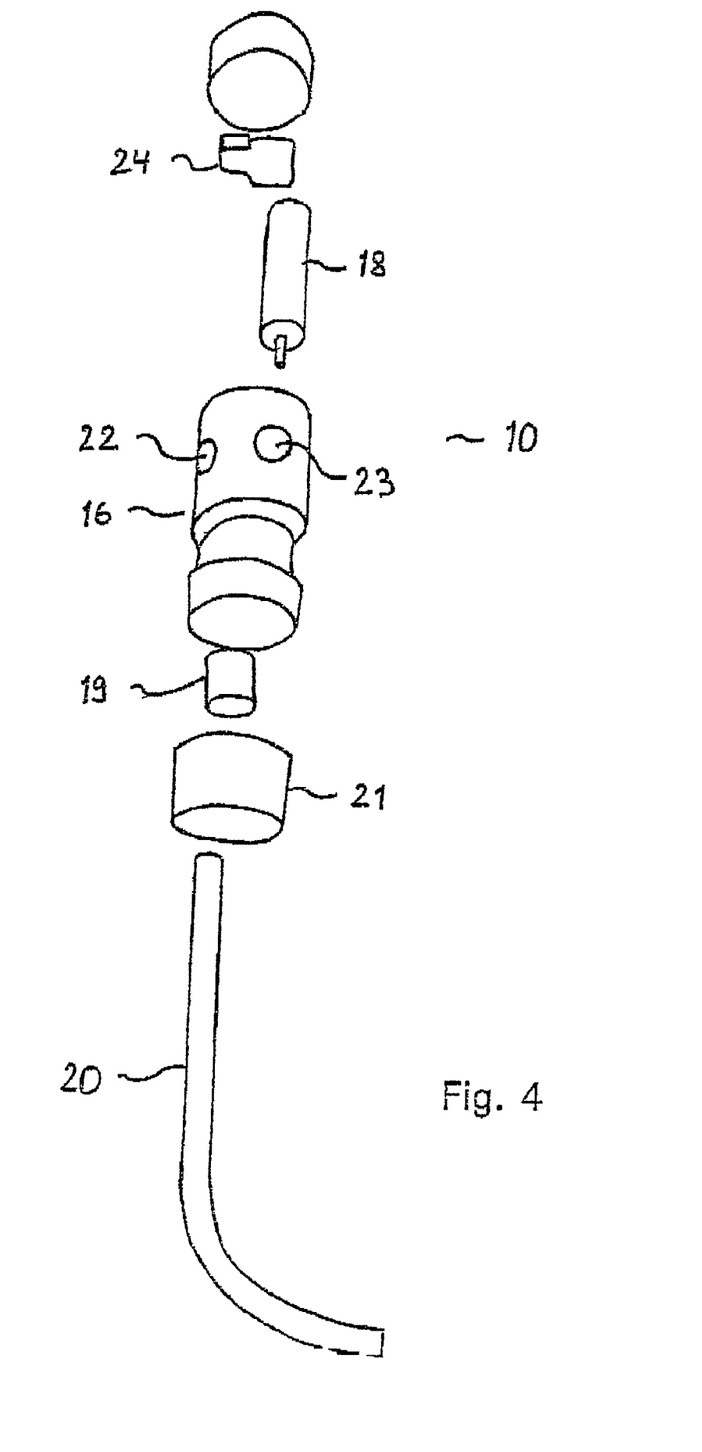
FIG. 4 shows a sketch of an agitator for a bioreactor.

FIG. 4 reveals an agitator 10 for use in a bioreactor 9. The agitator 10 has a cylindrical body 16 with a centric bore 17, into which an agitating motor 18 is inserted from above and a shaft coupling 19 is inserted from below. The agitating motor 18 is connected via the shaft coupling 19 to a bent agitating shaft 20 which is designed as a tube and which extends by means of a supporting bearing through a cone 21 connected to the body 16 at the lower end. The cone 21 has a standard grinding NS 29 on its outer surface, so that the agitator 10 can be used universally in the most common laboratory appliances made from glass.

The cone 21 assumes the essential task of sealing off the gas measurement system and of accommodating the releasable connection of the agitating shaft 20 to the agitating motor 18.

The shaft coupling 19, which can be screwed onto the motor shaft of the agitating motor 18, has a ball-type locking mechanism for receiving the agitating shaft 20. The ball mechanism locks opposite the direction of rotation of the agitating motor 18. By contrast, as a result of rotation in the direction of rotation of the agitating motor 18, the lock opens and the agitating shaft 20 can be removed. To receive the shaft coupling 19, the cone 21 has a milled-out portion which is also used at the same time for the transfer of scavenging gas out of the body 16 into the rotating shaft coupling 19. The scavenging gas is then conducted further on via bores in the shaft coupling 19 into the hollow agitating shaft 20. Then, with the agitator rotating, the scavenging gas can be introduced through the end, open at the bottom, of the agitating shaft 19 into the biomass. Moreover, the cone 21 takes over the transfer of the measurement gases from the bioreactor 9 into the body 16 of the motor carrier and the lower mounting and sealing off of the agitating shaft 20.

The body 16 has two lateral bores 22, 23 for the guidance of measurement gas and scavenging gas. These bores 22 and 23 are led outward in the upper third of the body 16 via quick-action gas connectors. For safety reasons, the measurement gas outlet 22 should have a gas connector open in the drawn-off state (plug) and the scavenging gas inlet 23 should have a gas connector closed in the drawn-off state (socket). Thus, with the gas conduits drawn off, excess pressure occurring in the bioreactor 9 can escape outward at any time and cannot pass into the scavenging gas bores. Moreover, the bioreactor 9 can thus be operated even without a scavenging gas conduit and only with a measurement gas connection.

The measurement gas conduit is connected to a Peltier cooling element 24 as a measurement gas cooler, in order to reduce the water vapor concentration in the measurement gas due to condensation. The thermal coupling of the hot side of the Peltier cooling element 24 preferably takes place to the head of the agitator 10 by means of a heat conduction film.

Figure 5:
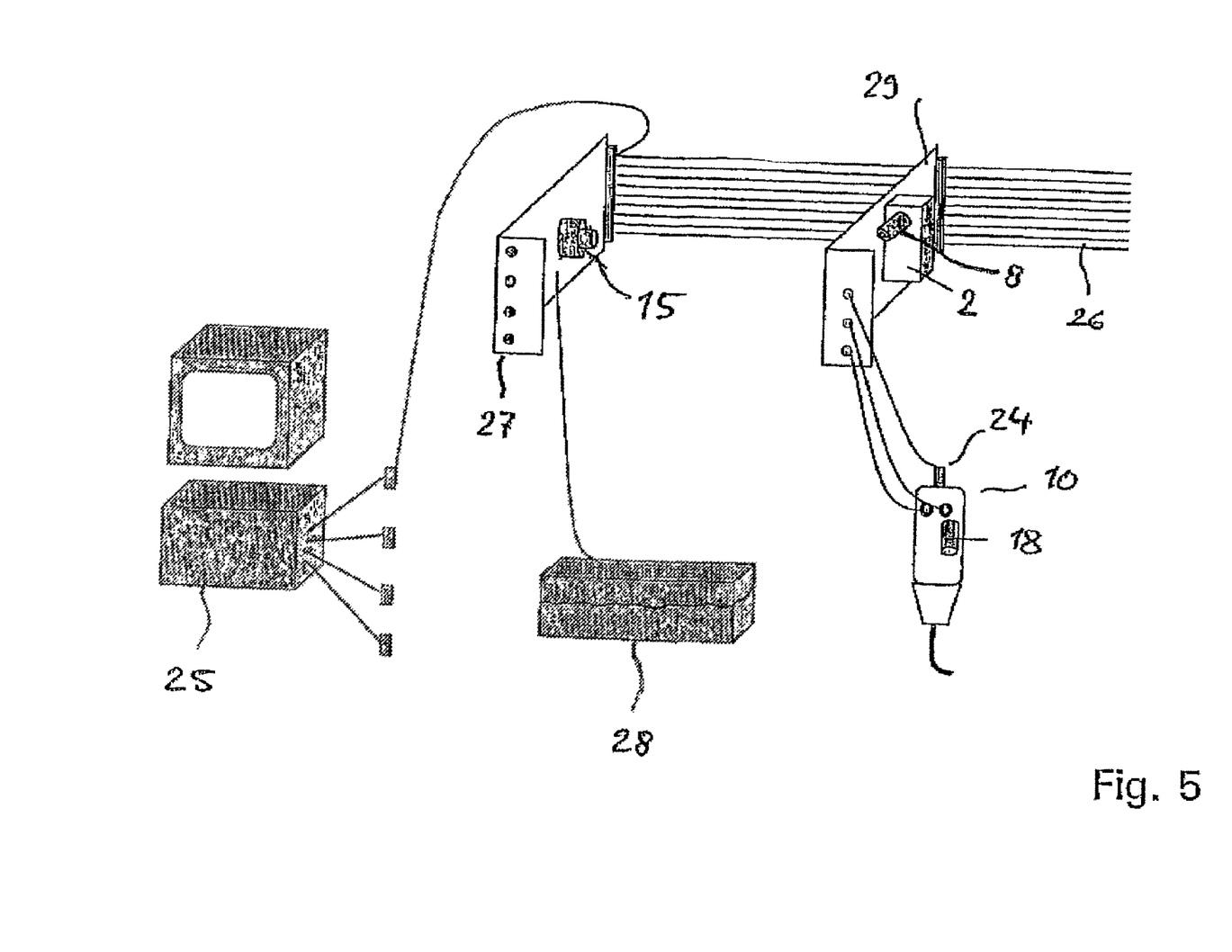
FIG. 5 shows a diagrammatic illustration of the individual subassemblies of the biogas measuring device according to the invention for the measurement of biogas volumes.

FIG. 5 indicates a sketch of individual subassemblies of a gas volume measurement system.

A control and evaluation computer 25 is connected via a bus 26, for example a serial bus (for example, RS232) to a control card 27 which carries the pressure sensor 15 for detecting the atmospheric pressure $P_a$. The control card 27 serves, moreover, for monitoring the temperature of a water bath 28 into which the bioreactor 9 is placed.

Furthermore, the computer 25 is connected via the bus 26 to a gas measurement module 29 which carries the gas volume meter 2 with the differential pressure sensor 8 and also the gas inlet and gas outlet valves 12, 13. The gas measurement module 29 forms, furthermore, an interface with the control and sensor outputs of the agitator 10 according to FIG. 4.

In particular, the Peltier cooling element 24 and the agitating motor 18 are activated, and, if appropriate, a temperature T-Peltier of the Peltier cooling element 24 is measured.

Figure 6:
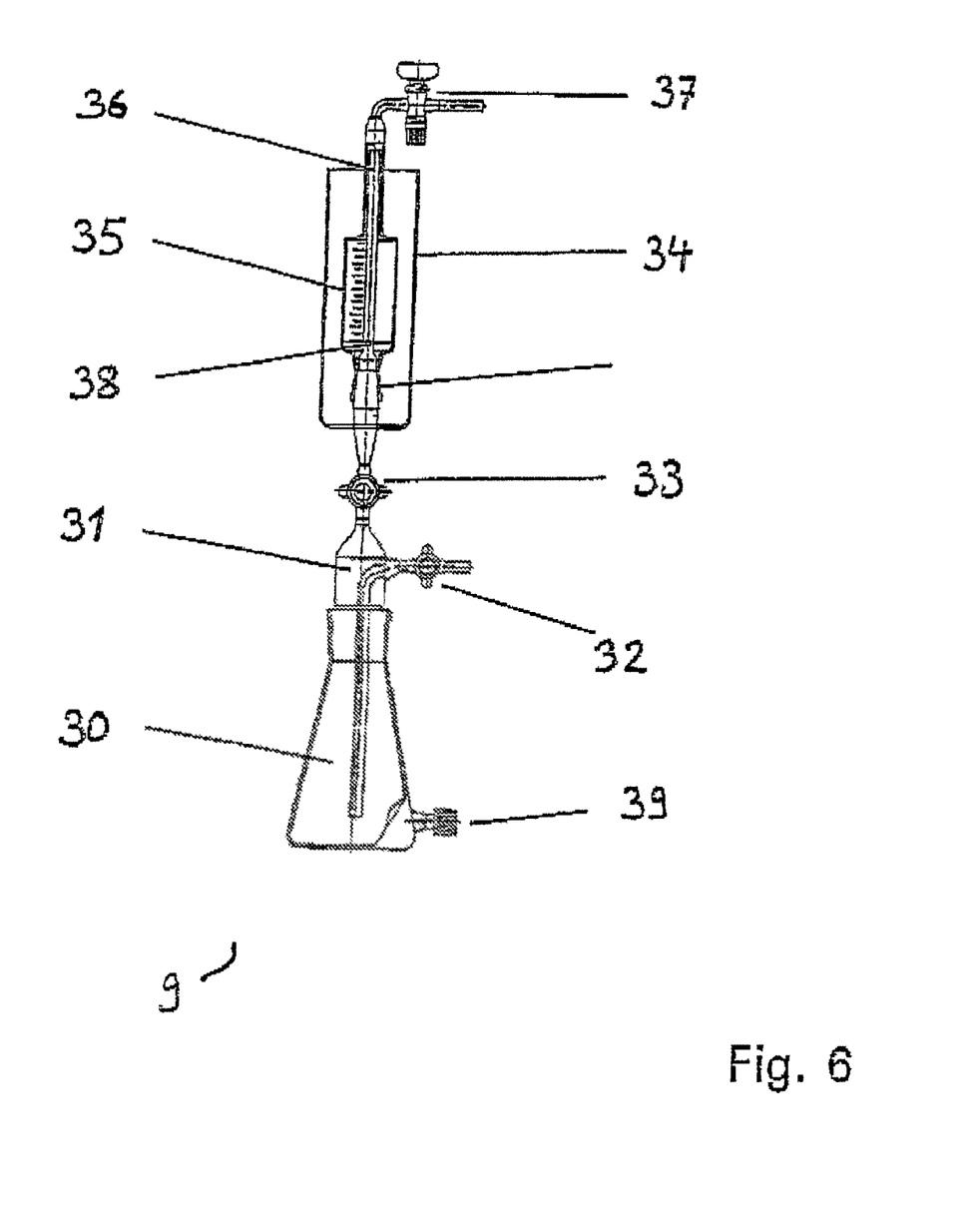
FIG. 6 shows a sketch of an exemplary embodiment of a fermentation measurement flask as a bioreactor.

FIG. 6 indicates a fermentation measurement flask as a bioreactor 9 for biogas measurement, which has an Erlenmeyer flask 30 as fermentation vessel. The Erlenmeyer flask 30 may be, for example, a 500 ml vessel with standard grinding NS45 at the connecting edge for a glass cone 31 inserted in the Erlenmeyer flask 30. The glass cone 31 has a nitrogen gasification valve 32 for scavenging the biogas reactor 9 with inert gas. A riser in the glass cone 31 is connected via a connecting valve 33 to a scaled gas collection measuring flask 35 arranged in a water equalizing vessel 34. A gastight connection is ensured by means of a standard grinding NS19 on the connecting surface of the scaled gas collection flask 35 and of the connecting valve piece 33. The gas which has accumulated in the scaled gas collection flask 35 is discharged via a gas riser pipe 36 and a venting valve 37 to the gas volume meter 2.

The scaled gas collection flask 35 has a water outlet orifice 38.

Furthermore, a septum 39 for sampling is provided in the Erlenmeyer flask 30.

After the bioreactor 9 has been put into operation and the connecting valve 33 and venting valve 37 have been opened, the gas collection flask 35 is filled via the water outlet orifice 38 with water located in the water equalizing vessel 34.

To set anaerobic test conditions, nitrogen is conducted via the nitrogen gasification valve 32 into biomass located in the Erlenmeyer flask 30. The nitrogen can escape from the biogas reactor 9 through the gas riser pipe 36 and the venting valve 37. The gasification and venting valves 32 and 37 are subsequently closed and gas measurement is started. In this case, the venting valve is connected to the gas volume meter and is opened again for continuous gas measurement.

The invention claimed is:
1. A biogas measuring device, comprising:
a bioreactor with an agitator therein,
a gas volume meter connected to the bioreactor via a gas conduit which permits biogas to be transported from the bioreactor to the gas volume meter, said gas volume meter comprising
a housing having a measuring chamber which has a defined measurement volume ($V_{REF}$),
a gas inlet valve controlling a gas inlet into the measuring chamber, a gas outlet valve controlling a gas outlet from the measuring chamber, a pressure sensor for detecting the atmospheric pressure ($P_a$), a differential pressure sensor for detecting a differential pressure (dP) between a gas pressure in the measuring chamber and atmospheric pressure ($P_a$) or a current system pressure ($P_2$), a measurement, control and evaluation unit for determining gas volumes measured by the gas volume meter for successive measurement cycles, wherein said measurement, control and evaluation unit is configured to operate said gas volume meter and said bioreactor to perform each measurement cycle according to the following steps i) introducing a gas quantity into the measuring chamber by opening the gas inlet valve until a defined threshold gas pressure is reached, then ii) closing of the gas inlet valve when the defined threshold gas pressure is reached, then iii) measuring temperature ($T_1$) in the measuring chamber, then iv) opening of the gas outlet valve for an expansion time, and then v) closing of the gas outlet valve (14), wherein the bioreactor is gastight, such that all gas volumes generated in the bioreactor are detected in the measuring chamber by the gas volume meter, a cooling element is provided on the gas conduit, and the measurement, control and evaluation unit controls the cooling element to reduce water vapor concentration in biogas transported from said bioreactor to said gas volume meter so that a measured gas volume of a measurement cycle is normalized to standard conditions.

2. The biogas measuring device as claimed in claim 1, wherein the measurement, control and evaluation unit controls measuring a current system pressure ($P_2$) during a measurement cycle and adapting the defined threshold gas pressure for a following measurement cycle with respect to the current system pressure ($P_2$).

3. The biogas measuring device as claimed in claim 2, wherein the defined threshold gas pressure set by said measurement, control and evaluation unit is about 2 hPa above the current system pressure ($P_2$).

4. The biogas measuring device as claimed in claim 1, wherein a heat capacity of the housing of the gas volume meter is higher than a heat capacity of said biogas and a mass of the housing is greater than a mass of said biogas.

5. The biogas measuring device as claimed in claim 1, further comprising steel wool filling the measuring chamber of the gas volume meter.

6. The biogas measuring device as claimed in claim 1, further comprising a scavenging gas valve for controlling a scavenging gas inlet in the measuring chamber of the gas volume meter for the introduction of a scavenging gas.

7. The biogas measuring device as claimed in claim 1, wherein said measurement, control and evaluation unit is configured to determine gas volume ($\Delta V$) of a measurement cycle from the atmospheric pressure ($P_a$), the differential pressure (dP) and the defined measurement volume ($V_{REF}$) according to the equation $$\Delta V = \left(\frac{P_a + dP}{P_a} - 1\right) V_{REF}.$$

8. The biogas measuring device as claimed in claim 1, wherein said measurement, control and evaluation unit is configured to calculate a gas volume ($\Delta V_n$) normalized to a standard pressure ($P_n$), according to the equation $$\Delta V_n = \frac{P_1 \cdot \Delta V}{P_n}$$

by means of measured pressure $P_1$ in the measuring chamber when the defined threshold gas pressure is reached.

9. The biogas measuring device as claimed in claim 1, further comprising a temperature sensor which is positioned to measure the temperature ($T_1$) of the measuring chamber.

10. The biogas measuring device as claimed in claim 9, wherein said measurement, control and evaluation unit is configured to calculate a gas volume ($\Delta V_n$) normalized to a standard temperature ($T_n$), according to the equation $$\Delta V_n = \frac{\Delta V_n = \Delta V \cdot T_n}{T_1}$$

by means of measured temperature ($T_1$) of the measuring chamber.

11. The biogas measuring device as claimed in claim 1, wherein the measurement, control and evaluation unit is configured to integrate gas volumes ($\Delta V$) determined in successive measurement cycles.

12. The biogas measuring device as claimed in claim 11, wherein said agitator has integrated gas conduits for biogas and scavenging gas, a cylindrical body with lateral bores for the gas conduits and a central bore for receiving an agitating shaft, an agitating motor received, gastight, in the cylindrical body, and a cone on the cylindrical body for gastight installation in the bioreactor, the gas conduit being connected to the gas volume meter.

13. The biogas measuring device as claimed in claim 12, wherein one of said gas conduits passes through a hollow shaft into the bioreactor.

14. The biogas measuring device as claimed in claim 1, wherein the cooling element is a Peltier cooling element.

15. A method for measuring biogas volumes generated by a bioreactor, comprising the steps:

cooling a biogas in a conduit between a bioreactor and a gas volume meter to reduce water vapor condensation in said biogas;

determining a measured gas volume in said gas volume meter for multiple cycles where, for each cycle, performing the steps of introducing a quantity of biogas into a measuring chamber by opening a the gas inlet valve until a defined threshold gas pressure is reached in the measuring chamber, then closing the gas inlet valve when the defined threshold gas pressure is reached, then measuring a temperature ($T_1$) in the measuring chamber, then opening of the gas outlet valve (14) for an expansion time, and l) closing of the gas outlet valve (14), and normalizing said measured gas volume of a measurement cycle to standard conditions.

16. The method as claimed in claim 15, further comprising the steps of measuring a current system pressure after the step of closing of the gas outlet valve and a standby phase and, adapting the defined threshold gas pressure for a following measurement cycle with respect to the current system pressure.

17. The method as claimed in claim 15, wherein the step of determining the measured gas volume makes a determination for each measurement cycle of said multiple cycles based on an atmospheric pressure ($P_a$), a differential pressure (dP) and a defined measurement volume ($V_{REF}$) according to the equation $$\Delta V = \left(\frac{P_a + dP}{P_a} - 1\right) V_{REF}.$$

18. The method as claimed in claim 15, wherein the step of determining the measured gas volume is performed by calculating a gas volume normalized to a standard pressure ($P_n$), according to the equation $$\Delta V_n = \frac{P_1 \cdot \Delta V}{P_n}$$

by means of a measured pressure $P_1$ in a measuring chamber of said gas volume meter when the defined threshold gas pressure is reached.

19. The method as claimed in claim 15, wherein the step of determining the measured gas volume is performed by calculating a gas volume normalized to a standard temperature ($T_n$), according to the equation $$\Delta V_n = \frac{\Delta V_n = \Delta V \cdot T_n}{T_1}$$

by means of a measured temperature ($T_1$) of a measuring chamber of the gas volume meter.

* * * * *